United States Patent
Su

(10) Patent No.: US 11,826,392 B2
(45) Date of Patent: Nov. 28, 2023

(54) PURIFICATION METHOD OF FUNGAL CELL WALL COMPOSITION

(71) Applicant: HONG SHENG PRECISION BIOTECH CO., LTD., Taichung (TW)

(72) Inventor: Ching-Hua Su, Taichung (TW)

(73) Assignee: HONG SHENG PRECISION BIOTECH CO., LTD., Taichung (TW)

( * ) Notice: Subject to any disclaimer, the term of this patent is extended or adjusted under 35 U.S.C. 154(b) by 0 days.

(21) Appl. No.: 17/657,021

(22) Filed: Mar. 29, 2022

(65) Prior Publication Data
US 2023/0310529 A1  Oct. 5, 2023

(51) Int. Cl.
| | |
|---|---|
| C08B 37/08 | (2006.01) |
| C08B 37/00 | (2006.01) |
| A61K 36/074 | (2006.01) |
| A61K 31/726 | (2006.01) |
| A61L 27/20 | (2006.01) |
| A61L 27/60 | (2006.01) |

(52) U.S. Cl.
CPC .......... *A61K 36/074* (2013.01); *A61K 31/726* (2013.01); *A61L 27/20* (2013.01); *A61L 27/60* (2013.01); *C08B 37/0003* (2013.01); *C08B 37/003* (2013.01); *C08B 37/0063* (2013.01); *A61K 2236/33* (2013.01)

(58) Field of Classification Search
None
See application file for complete search history.

(56) References Cited

U.S. PATENT DOCUMENTS 10,131,716 B2 * 11/2018 Tai ................. A61L 27/60

FOREIGN PATENT DOCUMENTS

| TW | 442496 | 6/2001 |
| TW | I620570 | 4/2018 |

* cited by examiner

*Primary Examiner* — Layla D Berry
(74) *Attorney, Agent, or Firm* — Muncy, Geissler, Olds & Lowe, P.C.

(57) ABSTRACT

A purification method of fungal cell wall composition includes following steps: (1) taking a residue of a fungus fruiting body underwent extraction process for obtaining extract thereof, wherein the extract contains terpenoids, sterols, polysaccharides, or a combination thereof, and the residue contains the cell wall of the fruiting body; (2) placing the residue into an aqueous percarbonate solution to form a mixture liquid, which is reacted at a first temperature for decolorizing the residue, wherein the concentration of the aqueous percarbonate solution ranges from 5 to 20% (w/v), and the first temperature ranges from 15 to 40° C.; (3) after the decolorization process, raising the temperature of the mixture liquid to a second temperature for the mixture liquid to react, so as to digest and decompose the residue, wherein the second temperature ranges from 80 to 100° C.; and (4) filtering the treated mixture liquid to obtain a purified product.

14 Claims, 1 Drawing Sheet

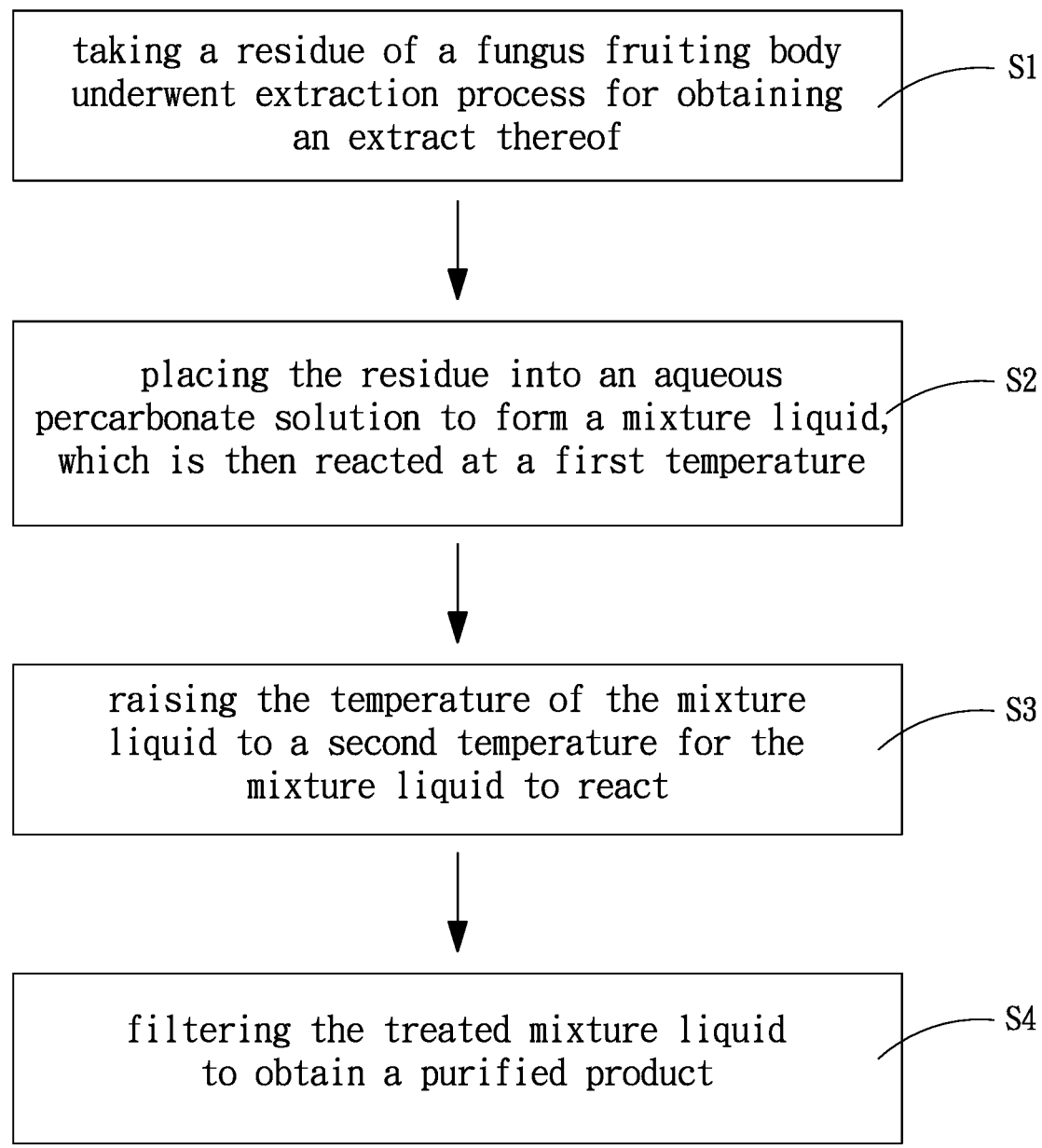

PURIFICATION METHOD OF FUNGAL CELL WALL COMPOSITION

BACKGROUND OF THE INVENTION

1. Field of the Invention

The present invention relates to processing techniques of fungus, and more particularly, to a purification method of fungal cell wall composition.

2. Description of the Related Art

*Ganoderma* is a fungus having multiple components, and also an important source of health care food. Its fruiting body contains about 1 to 3% of triterpenoids and sterols, and about 1 to 2% of water-soluble polysaccharides. Regarding a conventional method of extracting *Ganoderma*, a 65 to 95% alcohol is used for the first step of extraction. After low-polarity small-molecule triterpenoids and sterols are obtained, hot water is used for the second step of the extraction to obtain high-polarity macromolecular polysaccharides. The remaining *Ganoderma* residues, other than usage as excipients of the above-mentioned extracts, can only be used as soil conditioners and composts.

However, the aforementioned *Ganoderma* residues are mainly the cell wall of fruiting bodies of the *Ganoderma*, which still contain bountiful useful components including ultra-high molecular weight polysaccharides and chitin. Therefore, to effectively utilize those *Ganoderma* residues, TW Patent No. 442496 discloses the purified cell wall composition (a complex of chitin and polysaccharides) obtained through purification of the *Ganoderma* residues, which is a polyglucosamine fiber and has a copolymer structure of N-Acetylglucosamine and (1→3)-β-D-Glucan. Also, the experimental result shows that the polyglucosamine fiber can be used in skin wound dressings, cosmetics excipients, or pharmaceutical excipients.

According to the purification method of the TW Patent No. 442496 above, the first stage treatment is carried out with a strong base (1N sodium hydroxide), digesting and decomposing the residual protein, nucleic acid, and lipid of *Ganoderma* residue at high temperature 80 to 100° C.; afterward, the filtered material is rinsed. Then, in the second stage treatment, the material is treated with a decolorizer (0.1% hypochlorite), and the pigments of the *Ganoderma* residue is removed at a high temperature of 80 to 100° C., so as to become a white bifurcated pulp-like mycelial cell wall. However, such digestion and decomposition process using strong base would produce a large amount of extremely dark alkaline waste liquid, which is not only difficult to handle, but also causes a huge environment burden. Also, because hypochlorous acid is difficult to be removed, the decolorization process carried out with hypochlorite causes an issue of chlorine residue. Furthermore, the reaction conditions under the high temperature of hypochlorite are difficult to be controlled, thus easily causing over oxidation and resulting a poor recovery rate.

To improve the issue of poor recovery rate (only about 8 to 12%) of TW Patent No. 442496 above-mentioned, TW Patent No. 1620570 uses a 25 to 40% hydrogen peroxide to remove pigments in the second stage treatment. Although the recovery rate is increased to 25 to 35% (as shown in FIG. 2 and paragraph [0030] of TW Patent No. 1620570), the difficulties of over-oxidation and uneasily controlled reaction temperature remain. When the reaction is inadvertently treated, not only a large number of bubbles will be produced to overflow the reaction device, but also the recovery rate will sharply drop. Especially, High-concentration hydrogen peroxide is a highly toxic, reactive, corrosive, and oxidizing liquid, which brings a greater risk in large-scale operation and storage. In addition, the post-treatment waste liquid treated by this method still contains a large amount of unreacted hydrogen peroxide, and the issue of a large amount of strong alkaline waste liquid being produced by the first stage treatment remains unsolved. As a result, the waste liquid treatment still causes a great burden.

SUMMARY OF THE INVENTION

To improve the issues above, the present invention discloses a purification method of fungal cell wall composition. Therein, an aqueous percarbonate solution is applied as the treating agent which finishes the processes of decolorization and digestion and decomposition at once, so as to replace the two-stage treatment of prior arts which is respectively applied with sodium hydroxide and hypochlorite or hydrogen peroxide. The present invention not only lowers the burden of waste liquid treatment, but also increases the recovery rate of the purified product.

For achieving the aforementioned objectives, the purification method of the present invention comprises following steps:

(1) taking a residue of a fungus fruiting body underwent extraction process for obtaining an extract thereof, wherein the extract contains terpenoids, sterols, polysaccharides, or a combination thereof, and the residue contains the cell wall of the fruiting body;

(2) placing the residue into an aqueous percarbonate solution to form a mixture liquid, which is then reacted at a first temperature for decolorizing the residue, wherein a concentration of the aqueous percarbonate solution ranges from to 20% (w/v), and the first temperature ranges from 15 to 40° C.;

(3) after the decolorization, raising the temperature of the mixture liquid to a second temperature for the mixture liquid to react, so as to digest and decompose the residue, wherein the second temperature ranges from 80 to 100° C.; and (4) filtering the treated mixture liquid to obtain a purified product.

Therein, the aqueous percarbonate solution is an aqueous sodium percarbonate ($2Na_2CO_3 \cdot 3H_2O_2$) solution.

Therein, the extracting process in step (1) is orderly carried out with an organic solvent extraction for obtaining the extract containing triterpenoids and sterols, and a hot water extraction for obtaining the extract containing polysaccharides.

Therein, the fungus belongs to a type of *Ganoderma*, and the purified product is a complex of chitin and polysaccharides.

Therein, the purified product is a polyglucosamine fiber and is a copolymer structure of N-Acetylglucosamine and (1→3)-β-D-Glucan.

Therein, the purified product can be applied as skin wound dressings, cosmetics or care products excipients, or pharmaceutical excipients.

With such method, in step (2), the residue of fruiting bodies of *Ganoderma* is first treated with aqueous sodium percarbonate solution at room temperature, such that the aqueous sodium percarbonate solution gradually releases $H_2O_2$, thereby carrying out a decolorization reaction of the residue, wherein more sodium percarbonate can be added according to decolorization degree. After the decolorization finishes, temperature of the original reactant mixture liquid is raised in step (3). Because the sodium percarbonate releases sodium carbonate after added with water, and it can still provide sufficient alkalinity in a high-concentration and temperature rising condition, the digestion and decomposition reaction are allowed to be carried out for decomposing the protein, nucleic acid, and small amount of lipid in the *Ganoderma* residue, thereby assuring that there is no residue of allergenic component.

Therefore, the present invention applies the aqueous sodium percarbonate solution as the treating agent to finish the decolorization and digestion and decomposition processes at once, so as to replace the two-stage treatment of prior arts which is respectively applied with sodium hydroxide and hypochlorite or hydrogen peroxide. Also, because the decolorization reaction of the present invention is carried out at room temperature, the reaction is mild and does not cause over oxidation, so that the recovery rate of the purified product can be increased to about 50 to 60%. In addition, the purification method of the present invention only produces a waste liquid having a lighter color once in the overall process, and the waste liquid only contains sodium carbonate and a small amount of hydrogen peroxide. Thus, the method of the present invention reduces the burden of waste liquid treatment. Further, the sodium percarbonate is in a form of white powdery particles, which not only has a lower cost of usage, but also assures the safety during storage and utilizing process.

BRIEF DESCRIPTION OF THE DRAWINGS

The sole FIGURE is a flow chart of the method in accordance with an embodiment of the present invention.

DETAILED DESCRIPTION OF THE INVENTION

The aforementioned and further advantages and features of the present invention will be understood by reference to the description of the preferred embodiment in conjunction with the accompanying drawings.

Referring to the sole figure, the present invention provides a purification of fungal cell wall composition, comprising following steps.

Step (1): taking a residue of a fungus fruiting body underwent extraction process for obtaining an extract thereof. In various embodiment, the fungus in the present invention is a type of *Ganoderma*. The extraction process first takes a fruiting body of *Ganoderma* and breaks the fruiting body in pieces, and then immerses them in an organic solvent, so as to carry out an organic solvent extraction to obtain an extract containing triterpenoids and sterols. Therein, the organic solvent is selected from methanol, ethanol, or propanol, and is preferably ethanol (alcohol). Afterward, the residue after the extraction of the organic solvent is washed and immersed in hot water, so as to carry out a hot water extraction to obtain an extract containing polysaccharides. Finally, the residue after the reaction is washed, and dried at a temperature about 35 to 45° C.

Step (2): placing the residue from step (1) into an aqueous percarbonate solution to form a mixture liquid, which is then reacted at a first temperature for decolorizing the residue. In some embodiments, the aqueous percarbonate solution is an aqueous sodium percarbonate solution, with the concentration thereof ranging from 5 to 20% (w/v), preferably 7.5 to 15% (w/v); or preferably, the concentration of the aqueous percarbonate solution is 5, 7.5, 10, 12.5, 15, 17.5 or 20% (w/v); or preferably, the concentration of the aqueous percarbonate solution is 7.5 or 15% (w/v). In some embodiments, the first temperature ranges from 15 to 40° C., preferably 20 to 37° C.; or preferably, the first temperature is 15, 17.5, 20, 22.5, 25, 27.5, 30, 32.5, 35 or 37° C. Thus, in step (2), the residue of fruiting bodies of *Ganoderma* is treated with aqueous sodium percarbonate solution at room temperature, such that the aqueous sodium percarbonate solution gradually releases $H_2O_2$, thereby carrying out a decolorization reaction of the residue, wherein more sodium percarbonate can be added according to decolorization degree.

Step (3): after the decolorization, raising the temperature of the mixture liquid to a second temperature for the mixture liquid to react, so as to digest and decompose the residue. In some embodiments, the second temperature ranges from 80 to 100° C., preferably 85 to 90° C.; or preferably, the second temperature is 80, 82.5, 85, 87.5, 90, 92.5, 95, 97.5 or 100° C. Thus, the temperature of the original reactant mixture liquid is raised in step (3). Because the sodium percarbonate releases sodium carbonate after added with water, and it can still provide sufficient alkalinity in a high-concentration and temperature rising condition, the digestion and decomposition reaction are allowed to be carried out for decomposing the protein, nucleic acid, and small amount of lipid in the *Ganoderma* residue, thereby assuring that there is no residue of allergenic component.

Step (4), filtering the treated mixture liquid to obtain a purified product. In some embodiments, the purified product of the present invention is a complex of chitin and polysaccharides, which is a polyglucosamine fiber and has a copolymer structure of N-Acetylglucosamine and (1→3)-β-D-Glucan.

In some embodiments, the purified product is able to be washed and added into deionized water to form a suspension liquid. Afterward, the suspension liquid undergoes a pressure filtration with filter paper, so as to form a film on the filter paper. This film can be applied as skin wound dressings or excipients for cosmetic or skin care products. In some embodiments, the purified product can be rinsed and then processed, such as by freeze-drying, to be applied as an excipient for pharmaceutical tablets, thereby improving the physical properties of the powder during the tableting process.

Therefore, the purification method of the present invention applies the aqueous sodium percarbonate solution as the treating agent to finish the decolorization and digestion and decomposition processes at once, so as to replace the two-stage treatment of prior arts which is respectively applied with sodium hydroxide and hypochlorite or hydrogen peroxide. Also, because the decolorization reaction of step (2) of the present invention is carried out at room temperature, the reaction is mild and does not cause over oxidation, so that the recovery rate of the purified product can be increased to about 50 to 60%.

Further, the purification method of the present invention only applies the aqueous sodium percarbonate solution, so as to only produce a waste liquid having a lighter color once in the overall process, and the waste liquid only contains sodium carbonate and a small amount of hydrogen peroxide. Therefore, the method of the present invention reduces the burden of waste liquid treatment.

Specific embodiments of the present invention will be illustrated below.

Embodiment 1

The residue of fruiting body of *Ganoderma lucidum* which underwent alcohol and hot water extraction for obtaining triterpenoids, sterols and polysaccharides is acquired. Therein, the residue is mainly formed of macromolecules such as cell wall and protein, nucleic acid, and melanin. The residue has a weight of 100 equal parts (with 12.44% of moisture content); the residue is added into a 15% (w/v) sodium percarbonate solution of 1000 equal parts by volume, and is then placed in a room temperature ranging from 20 to 37° C. for reaction about 24 hours. Meanwhile, the aqueous sodium percarbonate solution gradually releases hydrogen peroxide and decolorizes the residue of *Ganoderma lucidum*. Afterward, the original reactant is heated to 85 to 90° C. for 1 to 2 hours to decompose the protein, nucleic acid, and the small amount of lipid in the residue of *Ganoderma lucidum*. Next, the residue is cooled down to normal temperature, and filtered to obtain a purified product, which is rinsed with water until the pH value thereof becomes neutral, and until the concentration of hydrogen peroxide is tested as not detectable with hydrogen peroxide test paper. The recovered purified product has a wet weight of 185.45 equal parts, a moisture content of 74.0%, and a recovery rate of 55.06%.

Embodiment 2

The residue of fruiting body of *Ganoderma lucidum* which underwent alcohol and hot water extraction for obtaining triterpenoids, sterols and polysaccharides is acquired. Therein, the residue has a weight of 100 equal parts (with 12.50% of moisture content); the residue is added into a 7.5% (w/v) sodium percarbonate solution of 1000 equal parts by volume, and is then placed in a room temperature ranging from 20 to 37° C. for reaction about 24 hours. Meanwhile, the aqueous sodium percarbonate solution gradually releases hydrogen peroxide and decolorizes the residue of *Ganoderma lucidum*. Because the decolorization is unable to be fully complete, sodium percarbonate of 75 equal parts by volume is further added, and the reactant is placed for another 24 hours for completing the decolorization. Afterward, the original reactant is heated to 85 to 90° C. for 1 to 2 hours to decompose the protein, nucleic acid, and the small amount of lipid in the residue of *Ganoderma lucidum*. Next, the residue is cooled down to normal temperature, and filtered to obtain a purified product, which is rinsed with water until the pH value thereof becomes neutral, and until the concentration of hydrogen peroxide is tested as not detectable with hydrogen peroxide test paper. The recovered purified product has a wet weight of 374.03 equal parts, a moisture content of 87.50%, and a recovery rate of 53.43%.

Embodiment 3

The residue of fruiting body of a *Ganoderma recinaceum* which underwent alcohol and hot water extraction for obtaining triterpenoids, sterols and polysaccharides is acquired. Therein, the residue has a weight of 100 equal parts (with 11.87% of moisture content); the residue is added into a 15% (w/v) sodium percarbonate solution of 1000 equal parts by volume, and is then placed in a room temperature ranging from 20 to 37° C. for reaction about 24 hours. Meanwhile, the aqueous sodium percarbonate solution gradually releases hydrogen peroxide and decolorizes the residue of *Ganoderma recinaceum*. Afterward, the original reactant is heated to 85 to 90° C. for 1 to 2 hours to decompose the protein, nucleic acid, and the small amount of lipid in the residue of *Ganoderma recinaceum*. Next, the residue is cooled down to normal temperature, and filtered to obtain a purified product, which is rinsed with water until the pH value thereof becomes neutral, and until the concentration of hydrogen peroxide is tested as not detectable with hydrogen peroxide test paper. The recovered purified product has a wet weight of 244.75 equal parts, a moisture content of 81.03%, and a recovery rate of 52.68%.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A purification method of fungal cell wall composition, comprising following steps:
   (S0) extracting a fungus fruiting body to obtain an extract;
   (S1) taking a residue of the extract, wherein the extract contains terpenoids, sterols, polysaccharides, or a combination thereof, and the residue contains the cell wall of the fruiting body;
   (S2) placing the residue into an aqueous percarbonate solution to form a mixture liquid, which is then reacted at a first temperature for decolorizing the residue, wherein a concentration of the aqueous percarbonate solution ranges from 5 to 20% (w/v), and the first temperature ranges from 15 to 40° C.;
   (S3) after the decolorization, raising the temperature of the mixture liquid to a second temperature for the mixture liquid to react, so as to digest and decompose the residue, wherein the second temperature ranges from 80 to 100° C.; and
   (S4) filtering the treated mixture liquid to obtain a purified product.

2. The purification method of claim 1, wherein the aqueous percarbonate solution is an aqueous sodium percarbonate solution.

3. The purification method of claim 1, wherein the concentration of the aqueous percarbonate solution ranges from 7.5 to 15% (w/v).

4. The purification method of claim 2, wherein the concentration of the aqueous percarbonate solution ranges from 7.5 to 15% (w/v).

5. The purification method of claim 1, wherein the concentration of the aqueous percarbonate solution is 7.5% (w/v) or 15% (w/v).

6. The purification method of claim 2, wherein the concentration of the aqueous percarbonate solution is 7.5% (w/v) or 15% (w/v).

7. The purification method of claim 1, wherein the first temperature ranges from 20 to 37° C.

8. The purification method of claim 1, wherein the second temperature ranges from 85 to 90° C.

9. The purification method of claim 1, wherein the extraction process is orderly carried out with an organic solvent extraction and a hot water extraction, wherein the organic solvent extraction is for obtaining the extract containing triterpenoids and sterols, and the hot water extraction is for obtaining the extract containing polysaccharides.

10. The purification method of claim 1, wherein the fungus belongs to a type of *Ganoderma*, and the purified product is a complex of chitin and polysaccharides.

11. The purification method of claim 10, wherein the complex is a copolymer structure of N-Acetylglucosamine and $(1\rightarrow3)$-$\beta$-D-Glucan.

12. The purification method of claim 1, wherein the purified product is able to be applied as skin wound dressings, cosmetics or care products excipients, or pharmaceutical excipients.

13. The purification method of claim 10, wherein the purified product is able to be applied as skin wound dressings, cosmetics or care products excipients, or pharmaceutical excipients.

14. The purification method of claim 11, wherein the purified product is able to be applied as skin wound dressings, cosmetics or care products excipients, or pharmaceutical excipients.

\* \* \* \* \*